(12) United States Patent
Raab et al.

(10) Patent No.: US 9,498,576 B2
(45) Date of Patent: Nov. 22, 2016

(54) DRIVE MECHANISM FOR A DRUG DELIVERY DEVICE

(75) Inventors: Steffen Raab, Frankfurt (DE);
Christopher James Smith, Holmes Chapel (GB);
(Continued)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 994 days.

(21) Appl. No.: 13/702,808

(22) PCT Filed: Jun. 9, 2011

(86) PCT No.: PCT/EP2011/059569
§ 371 (c)(1),
(2), (4) Date: Apr. 9, 2013

(87) PCT Pub. No.: WO2011/154484
PCT Pub. Date: Dec. 15, 2011

(65) Prior Publication Data
US 2013/0190697 A1    Jul. 25, 2013

(30) Foreign Application Priority Data

Jun. 11, 2010   (EP) .................................. 10165642

(51) Int. Cl.
*A61M 5/315*    (2006.01)
*A61M 5/24*    (2006.01)

(52) U.S. Cl.
CPC ........... *A61M 5/31543* (2013.01); *A61M 5/24* (2013.01); *A61M 5/3155* (2013.01);
(Continued)

(58) Field of Classification Search
CPC ............ A61M 5/31585; A61M 5/3155; A61M 5/31551; A61M 5/31553; A61M
(Continued)

(56) References Cited

U.S. PATENT DOCUMENTS 5,823,998 A    10/1998   Yamagata
5,827,232 A    10/1998   Chanoch et al.
(Continued)

FOREIGN PATENT DOCUMENTS

| EP | 0615762 | 9/1994 |
| EP | 1923085 | 5/2008 |
| WO | 99/38554 | 8/1999 |

OTHER PUBLICATIONS

International Preliminary Report on Patentability for Int. App. No. PCT/EP2011/059569, mailed Dec. 27, 2012.
(Continued)

*Primary Examiner* — Nathan R Price
*Assistant Examiner* — Anh Bui
(74) *Attorney, Agent, or Firm* — McDonnell Boehnen Hulbert & Berghoff LLP

(57) ABSTRACT

A drive mechanism for a drug delivery device which can be switched between a normal operation state and a reset state comprises of a housing having a proximal end and a distal end, a rotation member which is adapted to rotate in a first direction and in a second direction with respect to the housing, a drive member, wherein in the normal operation state the rotation member is coupled with the drive member so that the drive member follows rotational movement of the rotation member in the second direction, a piston rod, wherein in the normal operation state the piston rod is displaced in a distal direction with respect to the housing when the drive member rotates in the second direction with respect to the housing, a stop member, wherein in the normal operation state the stop member is coupled with the drive member so that the stop member prevents rotational move- (Continued)

ment of the drive member with respect to the housing in the first direction, and a separation member for switching the operation state, the separation member being adapted to move the stop member and the drive member in the distal direction with respect to the housing when the normal operation state is switched to the reset state, thereby decoupling the stop member and the drive member and decoupling the drive member and the rotation member.

15 Claims, 4 Drawing Sheets

(75) Inventors: Mark Philip Horlock, Timperley (GB); Stephen David Butler, Essington (GB)

(52) U.S. Cl.
CPC ....... *A61M 5/3158* (2013.01); *A61M 5/31551* (2013.01); *A61M 5/31553* (2013.01); *A61M 5/31555* (2013.01); *A61M 5/31583* (2013.01); *A61M 5/31585* (2013.01)

(58) Field of Classification Search
CPC ...................... 5/31555;A61M 5/31543; A61M 5/3158; A61M 5/31583
See application file for complete search history.

(56) References Cited

U.S. PATENT DOCUMENTS

| | | | |
|---|---|---|---|
| 2002/0111587 A1* | 8/2002 | Hommann | A61M 5/24 604/211 |
| 2004/0210199 A1* | 10/2004 | Atterbury | A61M 5/31566 604/224 |
| 2006/0153693 A1* | 7/2006 | Fiechter | A61M 5/31553 417/63 |

OTHER PUBLICATIONS

International Search Report for Int. App. No. PCT/EP2011/059569, completed Aug. 30, 2011.

* cited by examiner

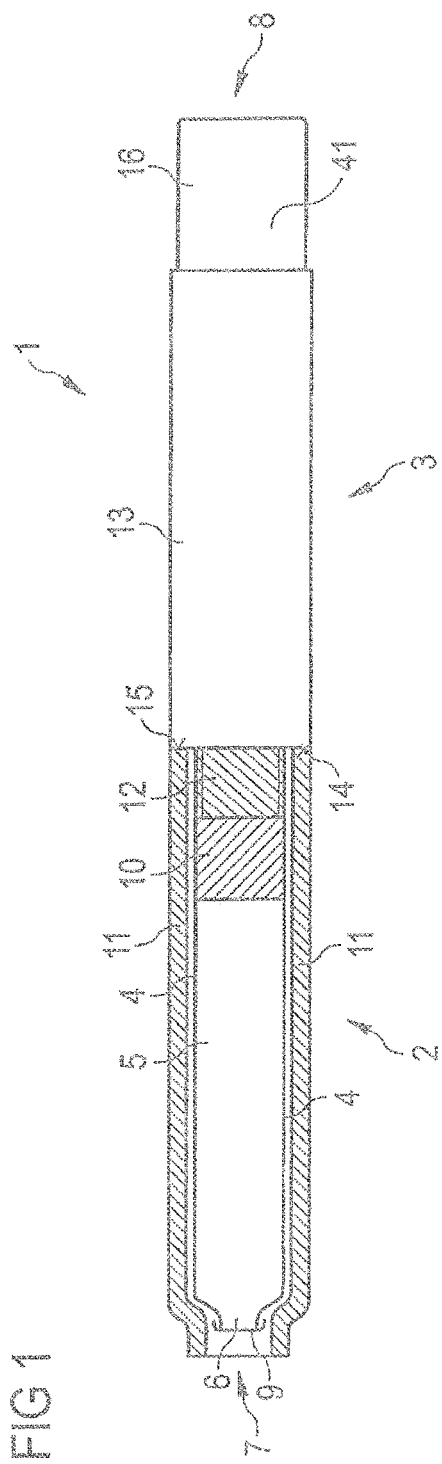

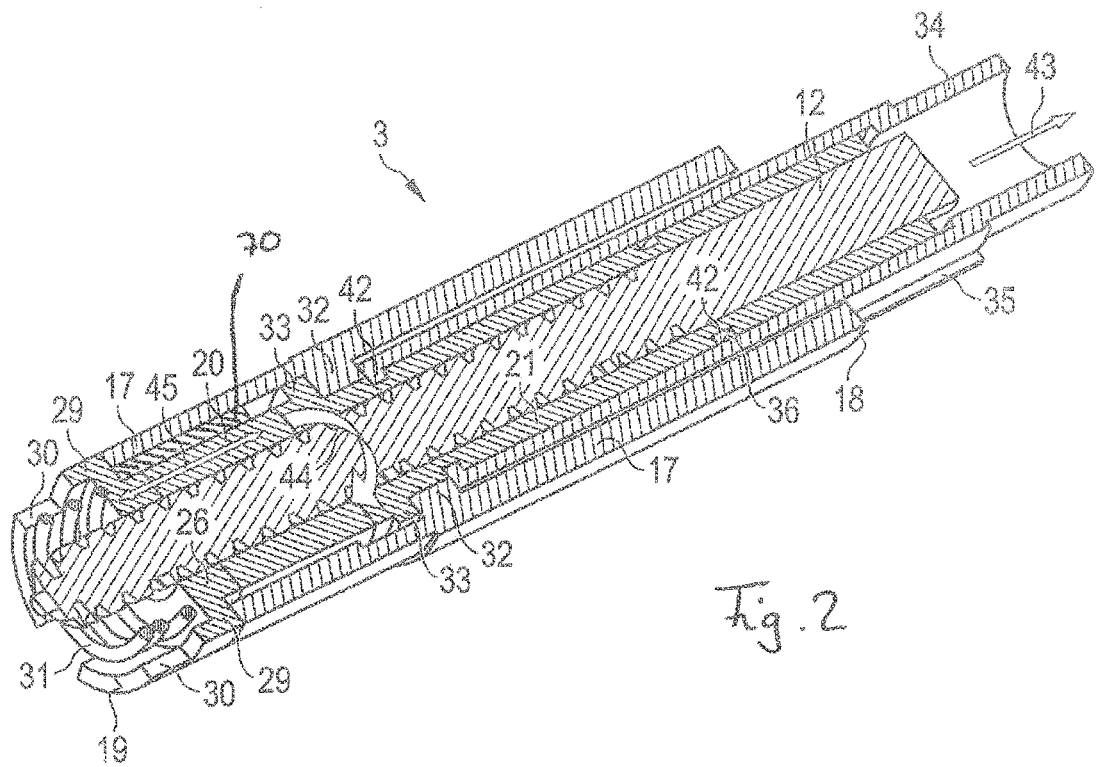
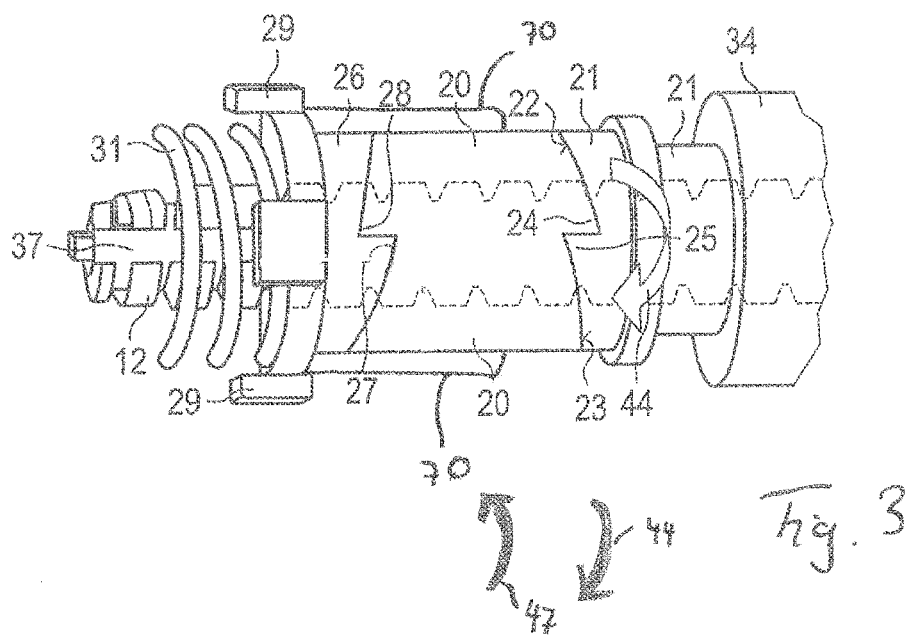

ial Application No.
DRIVE MECHANISM FOR A DRUG DELIVERY DEVICE

CROSS REFERENCE TO RELATED APPLICATIONS

The present application is a U.S. National Phase Application pursuant to 35 U.S.C. §371 of International Application No. PCT/EP2011/059569 filed Jun. 9, 2011, which claims priority to European Patent Application No. 10165642.9 filed on Jun. 11, 2010. The entire disclosure contents of these applications are herewith incorporated by reference into the present application.

FIELD OF INVENTION

The invention concerns a drive mechanism for a drug delivery device.

BACKGROUND

In a drug delivery device, a piston within a cartridge that contains a drug may be displaced with respect to the cartridge in the distal direction by a piston rod which moves in the distal direction with respect to the cartridge.

A fixed dose pen injector is a device that can be used to inject a number of set dose sizes from a pre-filled cartridge which may be made of glass. This may be ideally suited for chronic daily therapies where repeat doses of the same size are regularly required. The device may be disposable or reusable.

SUMMARY

It is an aim of the invention to provide a drive mechanism which can be reset, e.g. for use in a reusable drug delivery device.

For achieving this aim a drive mechanism for a drug delivery device which can be switched between a normal operation state and a reset state is provided. The drive mechanism comprises:

a housing having a proximal end and a distal end, a rotation member which is adapted to rotate in a first direction and in a second direction with respect to the housing, a drive member, wherein in the normal operation state the rotation member is coupled with the drive member so that the drive member follows rotational movement of the rotation member in the second direction, a piston rod, wherein in the normal operation state the piston rod is displaced in a distal direction with respect to the housing when the drive member rotates in the second direction with respect to the housing, a stop member, wherein in the normal operation state the stop member is coupled with the drive member so that the stop member prevents rotational movement of the drive member with respect to the housing in the first direction, and a separation member for switching the operation state, the separation member being adapted to move the stop member and the drive member in the distal direction with respect to the housing when the normal operation state is switched to the reset state, thereby decoupling the stop member and the drive member and decoupling the drive member and the rotation member.

In the normal operation state, mechanical interaction of stop member and drive member, for example interlocking, engagement, and/or abutment, during rotation of the rotation member in the first direction may prevent rotational movement of the drive member with respect to the housing in the first direction and, in particular, with respect to the stop member during setting of the dose. Thus, rotation of the drive member during dose setting can be avoided. The drive member may be coupled to the piston rod so as to convert its rotational movement in the second direction into distal movement of the piston rod with respect to the housing.

In the reset state, the stop member, the drive member and the rotation member are decoupled, which enables rotating the drive member and the piston in the first direction, thereby moving proximally the piston rod to an initial start position and enabling to insert a new cartridge.

A drug delivery device which comprises the above-mentioned drive mechanism can be reset easily by the user. Moreover, the device is reusable thus reducing waste.

In one embodiment the separation member is adapted to move the stop member in the distal direction with respect to the drive member when the separation member is moved in the distal direction with respect to the housing, thereby decoupling the stop member from the drive member.

In one embodiment the separation member is adapted to move the stop member and the drive member in the distal direction with respect to the rotation member when the separation member is moved in the distal direction with respect to the housing. In other words, the separation member is a means for moving the stop member and the drive member, thereby decoupling the stop, drive and rotation members.

One embodiment of the drive mechanism is suitable for being releasably connected with a cartridge holder, wherein the drive mechanism is switched to the reset state when the cartridge holder is detached from the drive mechanism.

When the user has dispensed the last dose of the medicament from the device, the user can then remove the cartridge holder and replace the cartridge, which may be formed e.g. as a glass vile, with a new one containing a drug. During this change the drive mechanism must be reset.

The drive mechanism separates and engages to enable device reset. The removal of the cartridge holder is the trigger for mechanism disengagement. Attaching the cartridge holder triggers the drive mechanism to be engaged.

One embodiment of the drive mechanism comprises a resilient member which is biased when the cartridge holder is attached to the drive mechanism and which is allowed to relax when the cartridge holder is detached, thereby moving the separation member in the distal direction with respect to the housing. Attaching the cartridge holder biases the resilient member, thereby coupling the stop member and the drive member as well as the drive member and the rotation member, so that the drive mechanism is switched to the normal operation mode.

In the reset state the piston rod is displaceable in the proximal direction with respect to the housing towards an axial start position, which enables to insert a new cartridge. In the normal operation state the piston rod is moveable in the distal direction with respect to the housing, thereby dispensing the drug. In one embodiment the piston rod can rotate freely when it is pushed; thereby rotating into the housing.

The drive mechanism may comprise a button which is coupled with the separation member, the button being moveable for switching to the reset mode. One embodiment which is switched between the operation states by attaching and detaching the cartridge holder may comprise the button for supporting the relaxing resilient member. This may be useful if the force, which is impacted by the relaxing member when the cartridge holder is detached, is not sufficient for decoupling the stop member, the drive member and the rotation member. The button could be used to control the drive mechanism disengagement. In another embodiment the button enables to switch the drive mechanism into the reset mode without detaching the cartridge holder, which enables to cancel a dose which is already set.

The button could be used as part of a cancel feature. If a user pulls the button and loads the device when a dispense dose is not required the device can be cancelled, which means that a set dose has not to be delivered. Without the cancel feature the user would have to waste the drug or carry the device in a loaded condition.

In one embodiment the drive member is rotationally decoupled from the rotation member when the button is moved in the distal direction with respect to the housing, which enables to cancel a dose which has been set.

In one embodiment, the separation member is located inside the housing and the button is located at least partly outside the housing, so that the user has access to the button.

In one embodiment the separation member comprises a first protrusion which engages with a trench in the drive member, the trench having a distal end. In the normal operation mode the first protrusion is positioned at a distance from the distal end of the trench. The first protrusion moves towards the distal end of the trench when switching to the reset state. This movement causes decoupling the drive member from the rotation member. The drive member is moved in the distal direction with respect to the housing when the first protrusion has reached the distal end of the trench and the separation member moves further in the distal direction with respect to the housing. One embodiment of the trench is formed circumferentially around the drive member so that the separating member does not stop the rotational movement of the drive member.

In one embodiment the separation member is coupled with the stop member, which enables to decouple the stop member from the drive member. In the normal state the stop member and the drive member may be coupled by a clutch which enables transferring rotational movement only in the second direction. In the reset mode the members are decoupled.

The term "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4
(1-39)-NH2,
H-(Lys)6-des Pro36, Pro37, Pro38 [Trp(O2)25, Asp28]
Exendin-4(1-39)-NH2,
H-Asn-(Glu)5-des Pro36, Pro37, Pro38 [Trp(O2)25, Asp28]
Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28]
Exendin-4(1-39)-(Lys)6-NH2,
H-Asn-(Glu)5-des Pro36, Pro37, Pro38 [Trp(O2)25, Asp28]
Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28]
Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28]
Exendin-4(1-39)-(Lys)6-NH2,
H-Asn-(Glu)5 des Pro36, Pro37, Pro38 [Met(O)14, Asp28]
Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25]
Exendin-4(1-39)-NH2,
H-(Lys)6-des Pro36, Pro37, Pro38 [Met(O)14, Asp28]
Exendin-4(1-39)-NH2,
H-Asn-(Glu)5-des Pro36, Pro37, Pro38 [Met(O)14, Trp(O2)
25, Asp28] Exendin-4(1-39)-NH2,
des Pro36, Pro37, Pro38 [Met(O)14, Trp(O2)25, Asp28]
Exendin-4(1-39)-(Lys)6-NH2,
H-(Lys)6-des Pro36, Pro37, Pro38 [Met(O)14, Trp(O2)25,
Asp28] Exendin-4(S1-39)-(Lys)6-NH2,
H-Asn-(Glu)5-des Pro36, Pro37, Pro38 [Met(O)14, Trp(O2)
25, Asp28] Exendin-4(1-39)-(Lys)6-NH2;
or a pharmaceutically acceptable salt or solvate of any one
of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Further features, refinements and expediencies become apparent from the following description of the exemplary embodiments in connection with the figures.

BRIEF DESCRIPTION OF THE FIGURES

FIG. 1 schematically shows a partly sectional side view of an exemplary embodiment of a drug delivery device.

FIG. 2 schematically shows a perspective sectional view of a part of a drive mechanism according to a first embodiment with schematically indicated movements of elements thereof during setting of a dose.

FIG. 3 schematically shows a more detailed side view of a part of FIG. 2.

DETAILED DESCRIPTION

Figures 4, 5:
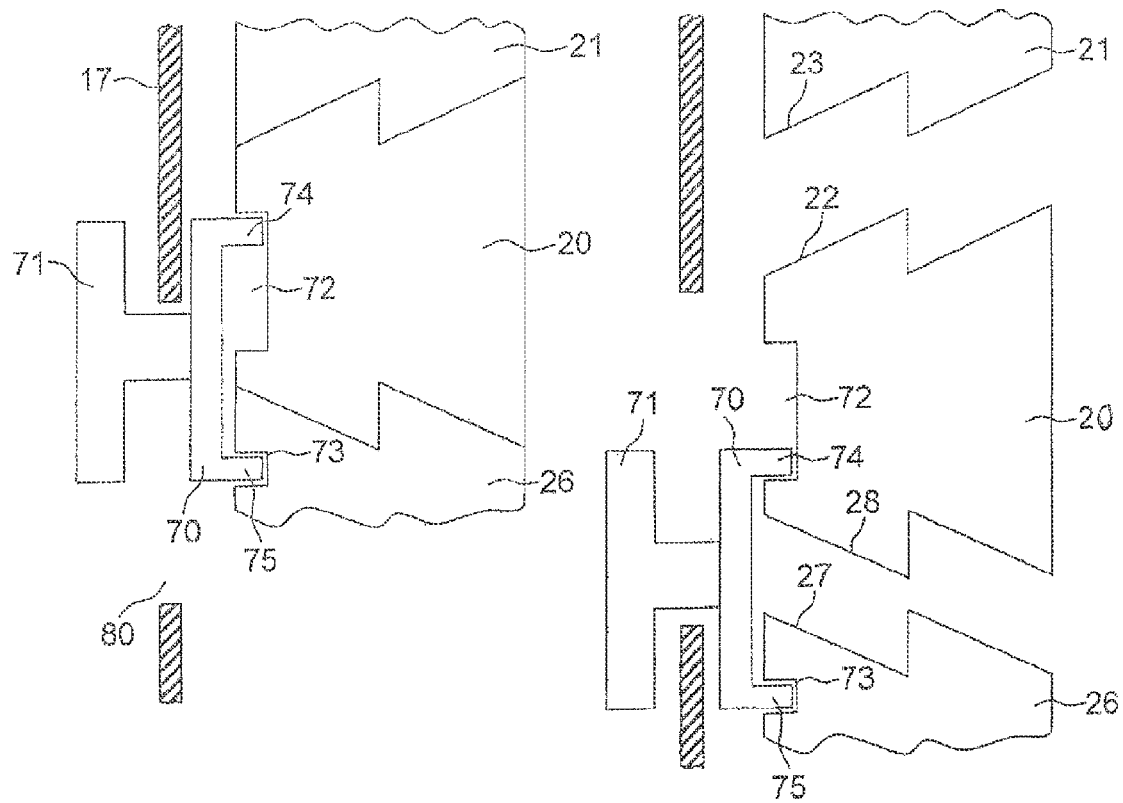
FIG. 4 shows a stop member, a drive member, a rotation member and a separation member of one embodiment of the drive mechanism in the normal operation mode.
FIG. 5 shows the stop member, the drive member, the rotation member and the separation member of the drive mechanism in FIG. 4 in the reset mode.

FIG. 1 shows a drug delivery device 1 which comprises a cartridge unit 2 and a drive unit 3. The cartridge unit 2 comprises a cartridge 4. Drug 5 is retained in the cartridge 4. The medication 5 is preferably liquid medication. The cartridge 4 preferably comprises a plurality of doses of the drug 5. The drug 5 may comprise insulin, heparin, or growth hormones, for example. The cartridge 4 has an outlet 6 at its distal end. Drug 5 can be dispensed from the cartridge through outlet 6. The device 1 may be a pen-type device, in particular a pen-type injector. The device 1 may be a disposable or a reusable device. The device 1 may be a device configured to dispense fixed doses of the medication or variable, preferably user-settable, doses. The device 1 may be a needle-based or a needle free device. The device 1 may be an injection device.

The term "distal end" of the drug delivery device 1 or a component thereof may refer to that end of the device or the component which is closest to the dispensing end of the device 1. The term "proximal end" of the drug delivery device 1 or a component thereof may refer to that end of the device or the component which is furthest away from the dispensing end of the device. In FIG. 1, the distal end of the device 1 is assigned reference numeral 7 and the proximal end of the device is assigned reference numeral 8.

The outlet 6 may be covered by a membrane 9, which protects the drug 5 against external influences during storage of the cartridge. For drug delivery, membrane 9 may be opened, e.g. pierced. For example, membrane 9 may be pierced by a needle unit (not explicitly shown). The needle unit may be (releasably) attached to the distal end of the cartridge unit 2. The needle unit may provide for fluid communication from the inside of the cartridge 4 to the outside of the cartridge through outlet 6.

A piston 10 is retained within the cartridge 4. The piston 10 is movable with respect to the cartridge. The piston 10 may seal the drug 5 within the cartridge. The piston 10 expediently seals the interior of the cartridge 4 proximally. Movement of the piston 10 with respect to the cartridge 4 in the distal direction causes drug 5 to be dispensed from the cartridge through outlet 6 during operation of the device.

The cartridge unit 2 furthermore comprises a cartridge retaining member 11. The cartridge 4 is retained within the cartridge retaining member 11. The cartridge retaining member 11 may stabilize the cartridge 4 mechanically. Additionally or alternatively, the cartridge retaining member 11 may be provided with a fixing member (not explicitly shown) for attaching the cartridge unit 2 to the drive unit 3.

The cartridge unit 2 and the drive unit 3 are secured to one another, preferably releasably secured. A cartridge unit 2 which is releasably secured to the drive unit 3 may be detached from the drive unit 3, for example in order to allow for providing for a new cartridge 4, if all of the doses of drug which once were in the cartridge formerly attached to the drive unit 3 have already been dispensed. The cartridge retaining member 11 may be releasably secured to the drive unit 3 via a thread, for example.

Alternatively, the cartridge retaining member 11 may be dispensed with. It is particularly expedient, in this case, to apply a robust cartridge 4 and to attach the cartridge directly to the drive unit 3.

The drive unit 3 is configured for transferring force, preferably user-exerted force, particularly preferably manually exerted force, to the piston 10 for displacing the piston 10 with respect to the cartridge 4 in the distal direction. A dose of medication may be dispensed from the cartridge in this way. The size of the delivered dose may be determined by the distance by which the piston 10 is displaced with respect to the cartridge 4 in the distal direction.

The drive unit 3 comprises a drive mechanism. The drive mechanism comprises a piston rod 12. The piston rod 12 may be configured for transferring force to the piston 10, thereby displacing the piston in the distal direction with respect to the cartridge 4. A distal end face of the piston rod 12 may be arranged to abut a proximal end face of the piston 10. A bearing member (not explicitly shown) may be arranged to advance the piston 10, preferably to abut the proximal end face of the piston 10. The bearing member may be arranged between piston 10 and piston rod 12. The bearing member may be fixed to the piston rod 12 or a separate member. If the piston rod 12 is configured to be rotated during operation of the device, for example during dose delivery, it is particularly expedient to provide for a bearing member. The bearing member may be displaced together with the (rotating) piston rod with respect to the housing. The piston rod may be rotatable with respect to the bearing member. In this way, the risk that the rotating piston rod drills into the piston and thereby damages the piston is reduced. Accordingly, while the piston rod rotates and is displaced with respect to the housing, the bearing member is preferably only displaced, i.e. does not rotate. The piston rod may be bounded by the bearing member.

The drive unit 3 comprises a housing 13 which may be part of the drive mechanism. The piston rod 12 may be retained in the housing. A proximal end side 14 of the cartridge unit 2 may be secured to the drive unit 3 at a distal end side 15 of the housing 13, for example via a threaded connection. Housing 13, cartridge 4 and/or cartridge retaining member 11 may have a tubular shape.

The term "housing" shall preferably mean any exterior housing ("main housing", "body", "shell") or interior housing ("insert", "inner body") which may have a unidirectional axial coupling to prevent proximal movement of specific components. The housing may be designed to enable the safe, correct, and comfortable handling of the medication delivery device or any of its mechanism. Usually, it is designed to house, fix, protect, guide, and/or engage with any of the inner components of the medication delivery device (e.g., the drive mechanism, cartridge, piston, piston rod), preferably by limiting the exposure to contaminants, such as liquid, dust, dirt etc. In general, the housing may be unitary or a multipart component of tubular or non-tubular shape.

The term "piston rod" shall preferably mean a component adapted to operate through/within the housing, which may be designed to transfer axial movement through/within the medication delivery device, preferably from the drive member to the piston, for example for the purpose of discharging/dispensing an injectable product. Said piston rod may be flexible or not. It may be a simple rod, a lead-screw, a rack and pinion system, a worm gear system, or the like. "piston rod" shall further mean a component having a circular or non-circular cross-section. It may be made of any suitable material known by a person skilled in the art and may be of unitary or multipart construction.

The drive unit 3 comprises a dose part 16. The dose part 16 is movable with respect to the housing 13. The dose part 16 may be movable in the proximal direction with respect to the housing for setting of a dose of the drug 5 which is to be delivered and in the distal direction with respect to the housing for delivery of the set dose. The dose part 16 is preferably connected to the housing 13. The dose part 16 may be secured against rotational movement with respect to the housing. The dose part 16 may be moved (displaced) between a proximal end position and a distal end position with respect to the housing 13 (not explicitly shown). The distance by which the dose part is displaced with respect to the housing during setting of the dose may determine a size of the dose. The proximal end position and the distal end position may be determined by a respective stop feature which may limit the proximal or distal travel of the dose member with respect to the housing. The device 1 may be a variable dose device, i.e. a device configured for delivering doses of medication of different, preferably user-settable, sizes. Alternatively, the device may be a fixed dose device.

The device 1 may be a manually, in particular non-electrically, driven device. The (user-applied) force which causes the dose part 16 to be moved with respect to the housing 13 in the distal direction may be transferred to the piston rod 12 by the drive mechanism. For this purpose, other elements of the drive mechanism may be provided which are not explicitly shown in FIG. 1. The drive mechanism is preferably configured to not move the piston rod 12 with respect to the housing 13 when the dose part is moved in the proximal direction with respect to the housing for setting of the dose.

Embodiments of a drive mechanism which are suitable to be provided in the medication delivery device 1 as it was described above are described in more detail below.

An embodiment of a drive mechanism which is suitable for being implemented in the medication delivery device 1 as described above is described in connection with the following figures.

The drive mechanism comprises a housing part 17. The housing part 17 has a proximal end 18 and a distal end 19. The housing part 17 may be (outer) housing 13 of FIG. 1, a part thereof or an insert within housing 13, which insert is preferably secured against rotational and axial movement with respect to housing 13. The housing part 17 may be an insert sleeve, for example. The insert sleeve may be snap-fitted or glued to housing 13, for example. The housing part 17 may have a tubular shape. Housing part 17 may comprise outer fixing elements, for example snap-fit elements, for fixing housing part 17 to housing 13.

The piston rod 12 is retained in the housing 13, preferably within housing part 17. The piston rod 12 is driven in the distal direction with respect to the housing part 17 during dose delivery.

The drive mechanism furthermore comprises a drive member 20. Drive member 20 is retained within the housing part 17. Drive member 20 is configured to transfer force, preferably torque, to the piston rod 12. The transferred force may cause the piston rod 12 to be displaced in the distal direction with respect to the housing part 17 for dose delivery.

Drive member 20 is rotatable with respect to housing part 17. The drive member 20 may engage the piston rod 12. Rotational movement of the drive member, for example rotational movement in a second direction may be converted into distal movement of the piston rod 12 with respect to the housing part 17. This is explained in more detail below.

The drive mechanism furthermore comprises a rotation member 21. The rotation member 21 is rotatable with respect to the housing part 17 in a first direction, in particular for setting of a dose of the medication, and in a second direction, in particular for delivering the set dose. The second direction is opposite to the first direction. The first direction may be counter-clockwise and the second direction may be clockwise as seen from the proximal end of the device, for example.

Drive member, rotation member and/or piston rod are preferably configured to be rotatable about a (common) rotation axis. The rotation axis may extend through drive member, rotation member and/or piston rod. The rotation axis may be the main longitudinal axis of the piston rod. The rotation axis may run between the proximal end and the distal end of the housing part 17.

The rotation member 21 is coupled to the drive member 20 by a uni-directional clutch mechanism, in particular a friction clutch mechanism. This clutch mechanism permits rotational movement of the rotation member 21 with respect to the drive member 20 when the rotation member rotates in the first direction with respect to the housing part 17. The clutch mechanism prevents rotational movement of the rotation member 21 with respect to the drive member 20, when the rotation member rotates in the second direction with respect to the housing part 17. The drive member 20 may thus follow rotational movement of the rotation member 21 in the second direction with respect to the housing part 17.

The drive member 20 is arranged to abut and/or engage the rotation member and, in particular, engages rotation member 21. The drive member 20 comprises a toothing 22. Toothing 22 may be provided at one end of the drive member, e.g. its proximal end. The rotation member comprises a toothing 23. Toothings 22 and 23 face one another. Toothing 23 may be provided at one end of the rotation member which end faces the drive member 20, e.g. at the distal end of the rotation member. Toothing 22 comprises a plurality of teeth 24. Toothing 23 comprises a plurality of teeth 25. Teeth 24 and/or 25 may extend and preferably may be oriented along the rotation axis. Toothings 22 and 23 may be configured to mate with one another. The rotation member and the drive member may engage each other by toothings 22 and 23 being in engagement.

A respective tooth of teeth 24 and/or teeth 25 may be ramp-shaped, in particular along the azimuthal (angular) direction as seen from the rotation axis. The ramp of the respective tooth is limited (in the angular direction) by a steep end face of that tooth, i.e. a face of the tooth that runs parallel to the rotation axis or includes a smaller angle with the rotation axis when projected on this axis than the ramp when projected on this axis. The steep end face is followed by the ramp of the next tooth.

The teeth 24 may be circumferentially disposed on the drive member 20, particularly at the end of the drive member 20 which faces the rotation member 21. The teeth 25 may be circumferentially disposed on the rotation member 21, particularly at the end of the rotation member 21 which faces the drive member 20.

When the steep end faces of two teeth abut and the rotation member is rotated further on in the second direction, the steep sides stay in abutment and drive member 20 follows the rotation of rotation member 21. When the rotation member rotates in the first direction, the ramp of the teeth—which ramps, in particular, run obliquely with respect to the rotation axis—slide along each other and, in consequence, the rotation member 21 may rotate with respect to the drive member 20.

The drive mechanism furthermore comprises a stop member 26. The drive member may be arranged between the stop member 26 and the rotation member 21. The stop member 26 is configured for preventing rotational movement of the drive member 20 in the first direction with respect to the housing part 17 during setting of a dose, i.e. when the rotation member rotates in the first direction. Thus, the rotation member 21 may rotate in the first direction with respect to the housing part 17, whereas the drive member 20 and the stop member 26 do not rotate.

The stop member 26 is coupled to the drive member 20 by another uni-directional clutch mechanism, in particular a friction clutch mechanism. This clutch mechanism prevents rotational movement of the drive member 20 with respect to the stop member 26 when the rotation member rotates 21 in the first direction with respect to the housing part 17. The clutch mechanism permits rotational movement of the drive member 20 with respect to the stop member 26, when the rotation member 21 rotates in the second direction with respect to the housing part 17.

Thus, the rotation member 21 may rotate with respect to the drive member 20 and the stop member 26 in the first direction during setting of the dose, with rotation of the drive member 20 being prevented by its interaction with the stop member 26, and rotation member 21 as well as drive member 20 may rotate with respect to the stop member 26 in the second direction during delivery of the dose.

The stop member 26 may be arranged to abut and/or engage the drive member 20 during setting of the dose and, preferably, during delivery of the dose. The stop member 26 has a toothing 27. Toothing 27 may be provided at one end of the stop member which faces the drive member, e.g. its proximal end. The teeth may be ramp-shaped with a steep side and a less steep ramp. The teeth may be azimuthally disposed along the stop member, in particular on the perimeter of the stop member.

Drive member 20 has a toothing 28. Toothing 28 may be provided at one end of the drive member which faces the stop member, e.g. the distal end of the drive member. The teeth of toothing 28 may extend and preferably may be oriented along the rotation axis. The teeth 24 and the teeth 28 of the drive member 20 are oppositely disposed. The teeth 24 may be configured corresponding to the teeth 25 of the rotation member 21. The teeth 28 may be configured corresponding to the teeth 27 of the stop member 26. Toothings 27 and 28 may face one another. Toothings 27 and 28 may mate with one another. Toothings 27 and 28, in particular the steep sides of the teeth, do cooperate, e.g. abut, for preventing rotation of the drive member 20 with respect to the housing part 17 and, in particular, with respect to the stop member 26 in the first direction.

Stop member 26 is preferably secured against rotational movement, particularly preferably permanently secured against rotational movement, with respect to the housing part 17. Stop member 26 may be fixed to the housing or integrated into the housing. Stop member 26 may be fixed against displacement with respect to the housing part 17 or displacement with respect to the housing part 17 may be allowed.

As it is illustrated in the present embodiment, stop member 26 is displaceable with respect to the housing but non-rotatable with respect to the housing part 17. For that purpose, one or a plurality of, preferably oppositely disposed, guide features, for example guide lugs 29, are provided in the stop member 26. The respective guide feature 29 engages a corresponding guide slot 30 which may be provided in the housing, e.g. in housing part 17. This can be seen in FIGS. 2 to 3. A guide feature 29 cooperates with a guide slot 30 to prevent rotational movement of the stop member with respect to the housing part 17, with axial movement of the stop member 26 with respect to the housing being allowed. The axial movement of the stop member 26 may compensate for play between components of the drive mechanism during operation.

From the group comprising drive member 20, stop member 26 and rotation member 21 one or more members, preferably two members or three members, may be axially displaceable with respect to the housing part 17 and, preferably, with respect to the piston rod 12. Therein, the drive member and another one of the recited members may be axially displaceable with respect to the housing. The remaining member may be secured against axial displacement or may also be axially displaceable during operation of the drive mechanism for medication delivery. Accordingly, if the drive member and the stop member are axially displaceable, the rotation member may be axially secured or axially displaceable and so on. Play between the components caused by relative (axial) movement of components of the clutch mechanism with respect to the housing can be compensated for in this way. The distance by which the respective components may be axially displaced with respect to the housing may correspond to the (maximum) depth of a tooth of the respective toothing 22 or 28 of the drive member. Alternatively, the distance may be greater than the (maximum) depth of a tooth of the respective toothing.

Furthermore, the drive mechanism comprises a resilient member 31, preferably a spring member. The resilient member 31 may be biased during medication delivery operation of the drive mechanism. The resilient member may provide for a force that tends to keep the drive member 20 in engagement with the stop member 26 and/or the rotation member 21. The force may be exerted along the rotation axis. In the situation shown in FIGS. 2 to 3, this force may be exerted in the proximal direction. The resilient member 31 may be a helical (coil) spring. The resilient member 31 may be a compression spring.

The resilient member 31 may keep the drive member 20 and the stop member 26 in (permanent) mechanical contact, e.g. in abutment, with each other during setting and delivery of a dose of the medication. Alternatively or additionally, the resilient member 31 may keep the drive member 20 and the rotation member 26 in (permanent) mechanical contact, preferably abutment, with each other during setting and delivery of a dose of the medication.

The resilient member 31 may be integrated within stop member 26 or a separate component. The resilient member 31 may be arranged on the distal end side of the stop member 26.

The drive mechanism furthermore comprises a support member 32. Support member 32 is expediently fixed against axial and rotational movement with respect to the housing part 17 or integrated into housing part 17. Support member 32 is arranged on that side of the drive member 20 which is remote from the stop member 26. Support member 32 may be a protrusion, for example a ring-like protrusion. Rotation member 21 may extend through an opening in support member 32. The support member 32 may provide for a counter force to the force which is exerted by the resilient member 31. Permanent abutment of the rotation member with the drive member and of the drive member with the stop member during setting and delivery of medication is facilitated in this way.

The rotation member 21 has an (radially) outwardly protruding member 33, for example a flange portion. The protruding member 33 is expediently provided for abutting support member 32, in particular the distal end side of support member 32.

The drive mechanism furthermore comprises a dose member 34. Dose member 34 may be dose part 16 or may be a part of the dose part 16 of FIG. 1. Dose member 34 is movable with respect to the housing in the proximal direction for setting of a dose and for delivery of the dose. For example, the dose member 34 may be moved in the proximal direction with respect to the housing part 17 during dose setting and in the distal direction with respect to the housing part 17 during dose delivery. The dose member 34 may engage the housing part 17 or, alternatively, another part of housing 13 (not explicitly shown). Dose member 34 is preferably secured against rotational movement with respect to the housing part 17. The dose member 34 may comprise a guide feature 35, for example a guide lug or a guide slot, that engages another guide feature, for example a guide slot or a guide lug, respectively, that is provided in the housing part 17 or the housing 13. The dose member 34 may be displaced with respect to housing part 17 preferably only axially along and/or rotationally around the rotation axis.

Dose member 34 may be moved in the proximal direction and in the distal direction with respect to rotation member 21. Dose member 34 is arranged to be couplable and is preferably (permanently) coupled to rotation member 21 such that movement of the dose member, e.g. in the proximal direction with respect to the housing part 17, for setting a dose of the medication is converted into rotational movement of the rotation member in the first direction and movement of the dose member, e.g. in the distal direction with respect to the housing part 17, for delivering the dose is converted into rotational movement of the rotation member 21 in the second direction opposite to the first direction.

The rotation member 21 may be provided with an (outer) thread 36. Thread 36 may be engaged with one of or a plurality of engagement members 42 of dose member 34. The respective engagement member may be arranged on the inside of the dose member. The respective engagement member may be a thread or a part of a thread, for example. Thus, dose member 34 and rotation member 21 may be threadedly coupled, in particularly threadedly engaged. The rotation member 21 may be arranged inside the dose member 21.

The rotation member 21, the drive member 20, the stop member 26 and/or the dose member 34 may be or may comprise a respective sleeve. The piston rod 12 may be arranged to be driven and, in particular, may be driven through one of, more of or all of those sleeves. The piston rod 12 may run through one of, more of or all of those sleeves.

The drive member 20 and the piston rod 12 are configured for rotational movement of the drive member 20 with respect to the housing being converted into rotational movement of the piston rod with respect to the housing. The drive member 20 may engage the piston rod 12. The piston rod 12 is displaceable with respect to the drive member 20 along a displacement axis. Presently, the displacement axis runs along the rotation axis. The drive member 20 may be splined to the piston rod 12, for example.

The piston rod 12 is threadedly coupled to the housing 13 and comprises an engagement track 37, preferably two oppositely disposed engagement tracks, on the outside. The (respective) engagement track 37 may interrupt thread. The (respective) engagement track 37 preferably extends along the axis along which the piston rod is displaceable with respect to the housing and, in particular, with respect to the drive member.

Rotational movement of the drive member 20 with respect to the housing may thus be converted into rotational movement of the piston rod 12 with respect to the housing and the rotational movement of the piston rod 12 is, on account of the threaded engagement of the piston rod and the housing (part), converted into movement of the piston rod with respect to the housing in the distal direction.

The dose part 16 may comprise a dose knob which may be configured to be gripped by a user. Dose knob 41 may be arranged and connected to the dose member 34 at the proximal end. Dose knob and dose member may be unitary.

In the following, operation of the present drive mechanism for delivering drug from the cartridge 4 of FIG. 1 is described.

To set a dose, a user may manually move dose member 34 in the proximal direction (arrow 43) with respect to the housing part 17. To do so, the user may grip the dose knob and pull it in the proximal direction. Dose member 34 moves proximally also with respect to the rotation member 21. Proximal movement of the rotation member is prevented by support member 32 which abuts protruding member 33 of rotation member 21. Consequently, the proximal movement of dose member 34 with respect to the housing part 17 is converted into rotational movement of the rotation member 21 in the first direction (arrow 44) with respect to the housing part 17, in particular on account of the threaded engagement of dose member 34 and rotation member 21. Thus, the rotation member 21 rotates in the first direction—counter-clockwise as seen from the proximal end of the rotation member—with respect to the housing. Rotation member 21 also rotates with respect to the drive member 20 and to the stop member 26. The drive member 20 is prevented from rotating in the first direction by interaction with the stop member 26, e.g. by interlocking of toothings 27 and 28. As the piston rod 12 is coupled to the drive member 20 and rotation in the first direction of the drive member would cause the piston rod to travel in the proximal direction, the piston rod 12 is prevented from being driven in the proximal direction by interaction of stop member 26 and drive member 20. By preventing the piston rod 12 from moving during dose setting dose accuracy can be increased.

When the rotation member 21 rotates in the first direction, the ramps of the teeth of toothing 23 of rotation member 21 slide along the ramps of the teeth of toothing 22. Thus, a tooth of the rotation member may index around the rotation axis until the tooth engages one of the next teeth of toothing 22 of drive member 20. The teeth of rotation member 21 slide along the ramps of the teeth of drive member 20. During this movement, drive member 20 and, in particular, stop member 26 are displaced along the rotation axis with respect to piston rod 12 and housing by a distance determined by, preferably equal to, the depth of a tooth of toothing 22, before a tooth of toothing 23 (totally) disengages that tooth of toothing 22. Afterwards, the tooth of the rotation member 21 engages the next tooth of toothing 22 and the force provided by resilient member 31 moves drive member 20 and, in particular, stop member 26 back along the rotation axis into the axial start position.

A tooth of the rotation member which engages the next tooth of the drive member may cause an audible and/or tactile feedback to the user.

The drive mechanism is suitable for a fixed dose device or a user settable dose device. The size of the fixed dose of medication which is to be delivered or the increments in which a user-settable dose may be varied by a user are preferably determined by the distribution of the teeth of the respective toothings in the drive member, rotation member and stop member. The rotation member may be rotated over more than one tooth (dose increment) of the drive member for a user-settable dose device and over one tooth (only) for a fixed dose device. The number of teeth in the drive member 20 over which the rotation member 21 rotates during dose setting determines the size of the dose which is actually delivered.

After the dose has been set, the dose part 16 and with it the dose member 34 is moved (pushed) by the user in the distal direction with respect to housing part 17. Thus, the dose member 34 is moved in the distal direction with respect to the housing part 17. The rotation member 21 accordingly rotates in the second direction, which is opposite to the first direction, with respect to the housing. Drive member 20 follows rotational movement of the rotation member in the second direction. Rotational movement of the drive member 20 in the second direction is converted into rotational movement of the piston rod 12 in the second direction, which movement, in turn, is converted into movement of the piston rod 12 in the distal direction. Accordingly, the piston 10 of FIG. 1 may be displaced in the distal direction with respect to the cartridge 4 and a dose of medication 5 is dispensed from the cartridge, the amount of which corresponds to the previously set dose.

During dose delivery, toothings 22 and 23 interlock and ramps of the teeth of toothing 28 of the drive member 20 slide along ramps of the teeth of toothing 27 of stop member 26. This movement is similar to that described above for the relative rotational movement of rotation member and drive member with opposite rotation direction. The stop member 26 is thereby displaced in the distal direction with respect to the drive member 20 by a distance corresponding to the depth of a tooth of toothing 27 in stop member 26. Resilient member 28 forces the stop member 26 back into the axial starting position, when the next tooth of toothing 28 is engaged by the respective tooth of toothing 27.

A tooth of the drive member which engages the next tooth of the stop member may cause an audible and/or tactile feedback to the user.

In a normal operation state the stop member, the drive member and the rotation member are coupled which enables the set and delivery operation described-above. In a reset state the stop member, the drive member and the rotation member are decoupled. The drive mechanism is switched between these modes by means of a separation member 70 which is moveable axially with respect to the housing 17.

To reset the drive mechanism the piston rod 12 must be returned in the distal direction back into the housing. This is impossible when the drive mechanism is engaged. The piston rod 12 has to rotate through the threaded engagement to the housing. The drive member 20 is splined to the piston rod 12 and would also rotate. The stop member 26 stops the drive member 20 from rotating whilst the toothing 27, 28 are engaged.

The piston rod 12 can be returned in the proximal direction when the drive mechanism is disengaged. The drive member 20 is free to rotate as there are no other components stopping this motion. If included a number sleeve (not shown) may be splined directly to the drive member 20. The number sleeve may run in a number sleeve thread which is fixed to the housing. The number sleeve always registers the dose position at which the piston rod 12 is. The dose member and the rotation member 26 may be adapted to one another such that the rotation member 26 may rotate only by one tooth for a fixed dose device and by more than one tooth for a variable dose device. Such dose counter can be incorporated and the number will register the piston rod position and indicate the number of doses left.

FIG. 4 shows a detailed view of the stop member 26, the drive member 20, the rotation member 21 and the separation member 70 in the normal operation mode.

This embodiment of the drive mechanism comprises a separation member 70 which is coupled with a button 71. The separation member 70 is located inside the housing 17, the button 71 extruding through a hole or trench 80 in the housing 17. The separation member 70 is axially moveable by axial movement of the button 71.

The separation member 70 comprises a first protrusion 74 which engages with a trench 72 in the drive member 20. The first protrusion 74 is axially moveable in the trench 72. A second protrusion 75 engages with a cavity 73 in the stop member 26. The travel of the second protrusion 75 with respect to the stop member 26 is less than the travel of the first protrusion 74 with respect to the drive member 20. Preferably the cavity 73 enables no or only small axial movement of the second protrusion 75. The trench 72 and the cavity 73 may be formed circumferentially, which enable rotation movement of the stop member 26 and the drive member 20 with respect to the button 71.

In the normal operation state the first protrusion 74 is positioned at a distance from the distal end of the trench 72. The drive mechanism is switched to the reset state by moving the button 71 in the distal direction with respect to the housing 17, thereby shifting the separation member 70 distally. The first protrusion 74 moves towards the distal end of the trench 72 when switching to the reset state; thereby moving the stop member 26 distally away from the drive member 20. Already in this state a dose may be cancelled because the toothings 27, 28 of the stop and the drive members 26, 20 are disengaged.

FIG. 5 shows a detailed view of the stop member 26, the drive member 20, the rotation member 21 and the separation member 70 in the reset mode.

When the first protrusion 74 has reached the distal end of the trench 72 and the separation member 70 moves further in the distal direction with respect to the housing 17, the drive member 20 is moved in the distal direction with respect to the housing 17; thereby decoupling the drive member 20 from the rotation member 21.

In one embodiment (not shown) the button 71 for controlling engagement and disengagement of the drive mechanism is attached to the rotation member 26 which cannot rotate but can slide in the axial direction. The button 71 runs in a slot in the housing 17. In a first position of the button 71, a spring lock compresses the drive mechanism together in the distal direction. The stop member 26 is forced against the drive member 20 which is forced against the rotation member 21.

The drive mechanism is switched to the reset state when the button 71 is moved in the distal direction. The button 71 may have a ratchet which would engage the button 71 into a positive location at a second position. When the button 71 is moved distally the toothings 27, 28 of the stop and drive members 26, 21 disengage. The spring lock forces the drive member 20 away from the rotation member. In this state the dosing button can be pulled out and pushed in and the mechanism would not drive the drive member as the toothings 27, 28 are disengaged. This could be used as a cancel position.

When the button 71 is moved further in the distal direction to a third position the rotation member moves against a stop member in the housing. All toothings 27, 28; 22, 23 are separated. The drive mechanism is disengaged. The springs that are in the device are sized such that they give the correct forces to separate the mechanism as required and also maintain the correct function throughout the full range of device use and life. The separation distance may be controlled by features in the housing 17. The button 71 controls the mechanism separation by positioning it to one of three positions.

Figures 6, 7:
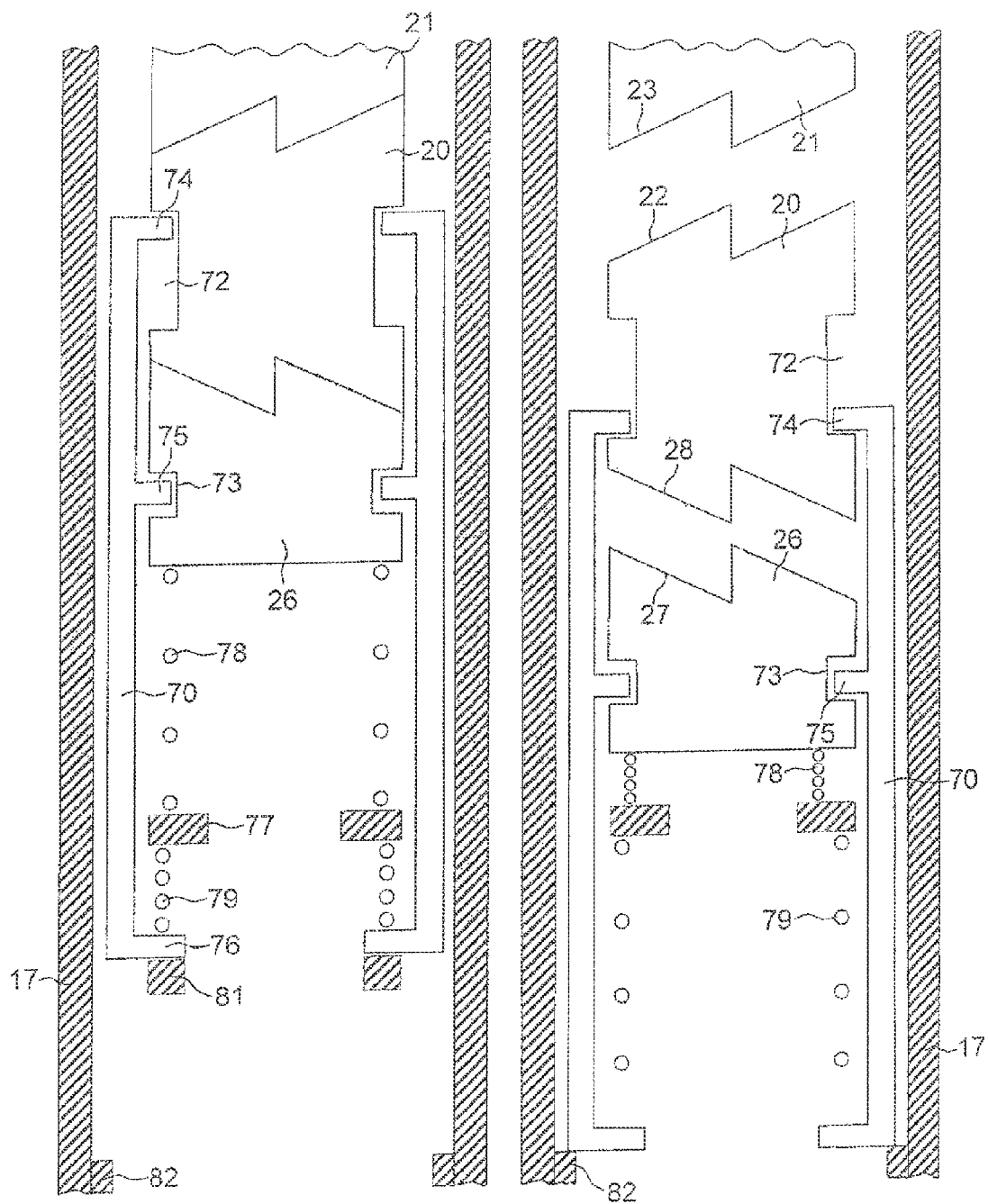
FIG. 6 shows the stop member, the drive member, the rotation member and the separation member of another embodiment of the drive mechanism in the normal operation mode.
FIG. 7 shows the stop member, the drive member, the rotation member and the separation member of the drive mechanism in FIG. 6 in the reset mode.

Turning now to FIG. 6, which shows a detailed view of the stop member 26, the drive member 20, the rotation member 21 and the separation member 70 in the normal operation mode of an embodiment having a drive mechanism switched between the operation states by attaching and detaching the cartridge holder.

The separation member 70 comprises a first protrusion 74 which engages with a circumferential trench 72 in the drive member. The first protrusion 74 is axially moveable in the trench 72. A second protrusion 75 engages with a circumferential cavity 73 in the stop member 26.

A first resilient member 78, e.g. a spring, is provided between the stop member 26 and a housing protrusion 77 which stops distal movement of the first resilient member 78. The first resilient member may be the resilient member 31 shown in FIG. 3. The spring force presses the stop member 26 towards the drive member 20; thereby coupling the stop member 26, the drive member 20 and the rotation member 21.

A second resilient member 79, e.g. a spring, is provided between the housing protrusion 77 and a third protrusion 76 of the separation member 70 which is located more distally than the housing protrusion 77. When the second resilient member 79 is relaxed, the separation member 70 is moved distally with respect to the housing 17; thereby rotationally decoupling the stop, drive and rotation members 26, 20, 21.

In the normal operation mode the separation member 70 is pushed to a first position by parts 81 of the cartridge holder (not totally shown in FIGS. 6 and 7) or another element of the device which is pushed distally by the attachment of the cartridge holder. The first protrusion 74 is positioned at a distance from the distal end of the trench 72. The second resilient member 79 is compressed by the attached cartridge holder.

When the cartridge holder is attached, the first resilient member 78 is forced into the distal direction. This releases the rotation member 26 which cannot rotate but can slide in the axial direction. The drive mechanism is pressed together in the distal direction. The stop member 26 is forced against the drive member 20 which is forced against the rotation member 21.

FIG. 7 shows the drive mechanism after detaching the cartridge holder. Detaching the cartridge holder causes relaxing of the second resilient member 79; thereby moving the separation member 70 distally with respect to the housing 17. The first resilient member 78 is compressed, when the second resilient member 79 relaxes. The first protrusion 74 moves towards the distal end of the trench 72 when switching to the reset state; thereby moving the stop member 26 distally away from the drive member 20. When the separation member 70 moves further in the distal direction with respect to the housing 17, the drive member 20 is moved in the distal direction with respect to the housing 17; thereby decoupling the drive member 20 and the rotation member 21. The distal movement of the separation member 70 may be stopped by a further protrusion 82 of the housing 17.

When the cartridge holder is removed the first resilient member 78 may be forced away from the stop member 26 in the proximal direction and the second resilient member 79 is extended. The second resilient member 79 pulls the stop member 26 in the proximal direction. In one embodiment the housing comprises a protrusion which stops the distal movement of the rotation member 26 (not shown in FIGS. 6 and 7). The separation member 70 serves as sliding clip retention feature. This separates the toothings 27, 28; 22, 23 when at the same time the second resilient member 79 forces the drive member 20 away from the rotation member 21. In one embodiment the housing comprises a protrusion which stops the distal movement of the drive member 20 (not shown in FIGS. 6 and 7). When the toothings 27, 28; 22, 23 are separated, the drive mechanism is disengaged. The resilient members 78, 79 that are in the device are sized such that they give the correct forces to separate the mechanism as required and also maintain the correct function throughout the full range of device use and life. The separation distance is controlled by features in the housing 17 and/or by the arrangement of the protrusions 74, 75, 76 of the separation member 70 and their distance from each other. The distance separation is such as to enable correct function during dosing and reset of the device life.

A button as described in connection with the FIGS. 4 and 5 can be additionally incorporated and used for a dose setting cancel operation.

It is mentioned that the features of the embodiments can be combined.

The invention claimed is:

1. A drive mechanism for a drug delivery device which can be switched between a normal operation state and a reset state, the drive mechanism comprising:
   a housing having a proximal end and a distal end,
   a rotation member which is adapted to rotate in a first direction and in a second direction with respect to the housing,
   a drive member, wherein in the normal operation state the rotation member is coupled with the drive member so that the drive member follows rotational movement of the rotation member in the second direction,
   a piston rod, wherein in the normal operation state the piston rod is displaced in a distal direction with respect to the housing when the drive member rotates in the second direction with respect to the housing,
   a stop member, wherein in the normal operation state the stop member is coupled with the drive member so that the stop member prevents rotational movement of the drive member with respect to the housing in the first direction, and
   a separation member for switching the operation state, the separation member being adapted to move the stop member and the drive member in the distal direction with respect to the housing when the normal operation state is switched to the reset state, thereby decoupling the stop member and the drive member and decoupling the drive member and the rotation member.

2. The drive mechanism according to claim 1, wherein the separation member is adapted to move the stop member in the distal direction with respect to the drive member when the separation member is moved in the distal direction with respect to the housing.

3. The drive mechanism according claim 1, wherein the separation member is adapted to move the stop member and the drive member in the distal direction with respect to the rotation member when the separation member is moved in the distal direction with respect to the housing.

4. The drive mechanism according to claim 1 suitable for being releasably connected with a cartridge holder, wherein the drive mechanism is switched to the reset state when the cartridge holder is detached from the drive mechanism.

5. The drive mechanism according to claim 4 comprising a resilient member which is biased when the cartridge holder is attached to the drive mechanism and which is allowed to relax when the cartridge holder is detached, thereby moving the separation member in the distal direction with respect to the housing.

6. The drive mechanism according to claim 1, wherein in the reset state the piston rod is displaceable in the proximal direction with respect to the housing towards an axial start position, in the normal operation state the piston rod is moveable in the distal direction with respect to the housing.

7. The drive mechanism according to claim 1, further comprising a button which is coupled with the separation member, the button being moveable for switching to the reset mode.

8. The drive mechanism according to claim 7, wherein the separation member is located inside the housing and wherein the button is located at least partly outside the housing.

9. The drive mechanism according to claim 7, wherein the drive member is rotationally decoupled from the rotation member when the button is moved in the distal direction with respect to the housing.

10. The drive mechanism according to claim 1, wherein the separation member comprises a first protrusion which engages with a trench having a distal end in the drive member, in the normal operation mode the first protrusion is positioned at a distance from the distal end of the trench, the first protrusion moving towards the distal end of the trench when switching to the reset state.

11. The drive mechanism according to claim 10, wherein the drive member is moved in the distal direction with respect to the housing when the first protrusion has reached the distal end of the trench and the separation member moves further in the distal direction with respect to the housing.

12. The drive mechanism according to the claim 10, wherein the trench is formed circumferentially around the drive member.

13. The drive mechanism according to claim 1, wherein the separation member is coupled with the stop member.

14. The drive mechanism according to claim 1, wherein in the normal state the stop member and the drive member are coupled by a clutch which enables transferring rotational movement only in the second direction.

15. The drive mechanism according to claim 1, when the stop member is decoupled from the drive member and the drive member is decoupled from the rotation member, the drive member and the piston rod are rotatable in the first direction to move the piston rod in the proximal direction.

\* \* \* \* \*